(12) United States Patent
Yang et al.

(10) Patent No.: US 6,461,326 B1
(45) Date of Patent: Oct. 8, 2002

(54) FLUORESCENT DYED ADHESIVE FOR BONDING VARIOUS COMPONENTS IN A MEDICAL DEVICE

(75) Inventors: Dahuan Yang, Plymouth; Joel Stanslaski, New Hope; Liguang Tang, Plymouth; Joseph Guaire Mary Scanlon, Crystal, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 39 days.

(21) Appl. No.: 09/696,852

(22) Filed: Oct. 26, 2000

(51) Int. Cl.[7] .............................................. A61M 29/00
(52) U.S. Cl. .................. 604/96.01; 250/461.1
(58) Field of Search ..................... 604/96.01; 623/1.11; 600/2; 606/2

(56) References Cited

U.S. PATENT DOCUMENTS

| | | | |
|---|---|---|---|
| 3,699,076 A | 10/1972 | Thomsen et al. | 524/719 |
| 4,003,382 A | 1/1977 | Dyke | 604/103 |
| 4,035,334 A | 7/1977 | Davydov et al. | 424/78.06 |
| 4,062,827 A | 12/1977 | Zollman | 524/718 |
| 4,251,305 A | 2/1981 | Becker et al. | 156/86 |
| 4,405,750 A | 9/1983 | Nakata et al. | 524/717 |
| 4,436,924 A | 3/1984 | Ashby et al. | 556/416 |
| 4,661,095 A | 4/1987 | Taller et al. | 604/103 |
| 4,751,020 A | 6/1988 | Marten et al. | 252/301.21 |
| 4,778,999 A | * 10/1988 | Fisher | 209/578 |
| 4,913,701 A | 4/1990 | Tower | 604/103 |
| 4,943,278 A | 7/1990 | Euteneuer et al. | 604/96 |
| 5,217,482 A | 6/1993 | Keith | 606/194 |
| 5,403,591 A | 4/1995 | Tighe et al. | 424/445 |
| 5,501,759 A | 3/1996 | Forman | 156/272.8 |
| 5,569,184 A | 10/1996 | Crocker et al. | 604/53 |
| 5,738,667 A | 4/1998 | Solar | 604/280 |
| 5,792,106 A | 8/1998 | Mische | 604/96 |
| 5,911,715 A | 6/1999 | Berg et al. | 604/525 |
| 5,944,726 A | 8/1999 | Blaeser et al. | 606/108 |
| 5,957,930 A | 9/1999 | Vrba | 606/108 |
| 5,968,069 A | 10/1999 | Dusbabek et al. | 606/194 |
| 5,997,562 A | 12/1999 | Zadno-Azizi et al. | 606/194 |
| 6,013,728 A | 1/2000 | Chen et al. | 525/92 A |
| 6,068,634 A | 5/2000 | Larentzen et al. | 606/108 |
| 6,099,497 A | 8/2000 | Adams et al. | 604/96.01 |
| 6,102,890 A | 8/2000 | Stivland et al. | 604/96 |

FOREIGN PATENT DOCUMENTS

| | | |
|---|---|---|
| WO | 97/31051 | 8/1997 |
| WO | 97/32624 | 9/1997 |

OTHER PUBLICATIONS

U.S. patent application Ser. No. 08/926,905, Ferrera et al., filed Sep. 10, 1997.

Shantha, K. L. et al . . . , "Developments and applications of cyanoacrylate adhesives," *J. Adhesion Sci Technol*, 3:237–260 (1989).

* cited by examiner

*Primary Examiner*—Edward K. Look
*Assistant Examiner*—Dwayne J. White
(74) *Attorney, Agent, or Firm*—Vidas, Arrett & Steinkraus P.A.

(57) ABSTRACT

An intraluminal medical device comprised of two or more substrates formed of the same or a different material wherein the substrates are bonded together using a fluorescent dyed adhesive.

22 Claims, 2 Drawing Sheets

FLUORESCENT DYED ADHESIVE FOR BONDING VARIOUS COMPONENTS IN A MEDICAL DEVICE

FIELD OF THE INVENTION

This invention relates to the use of adhesive systems comprising a fluorescent dye for various bonding applications in an intraluminal medical device, in particular the catheter assembly or stent delivery system. The fluorescent adhesive allows for easy and non-destructive inspection of the bond quality, as well as allowing easy determination of imperfections or tears in the balloon material.

BACKGROUND OF THE INVENTION

Adhesives are used for a variety of applications in the manufacture of catheter assemblies. One such application involves mounting a balloon on a catheter assembly. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure is supplied to the balloon through an inflation lumen in the catheter, thereby expanding the balloon.

The bonding of a catheter balloon to a catheter in particular requires that the adhesive form an excellent seal between the balloon and the catheter. This is due to the fact that once properly positioned within a patient's body vessel, the balloon is inflated by filling it with inflation fluid under high pressure which the adhesive seal must be able to withstand. An improper or poor seal may result in leakage of inflation fluid into the patient, inability to achieve the proper inflation pressure, and even deflation of the balloon due to pressure loss thus requiring that the procedure be repeated.

A number of methods for sealing a balloon to a catheter are currently known in the art. U.S. Pat. No. 4,913,701 to Tower describes a method of bonding a polyurethane balloon to a polyethylene catheter using a cyanoacrylate adhesive. U.S. Pat. No. 4943278 to Euteneuer, et al. also describes a method of mounting a balloon member to a catheter by bonding, such as by an epoxy. U.S. Pat. No. 4661095 to Taller et al. describes bonding polyurethane balloons to catheters formed of thermoplastic polyurethane using special polyurethane adhesives.

There are numerous other applications in the manufacture of catheter assemblies where adhesives and/or fusion methods are used to adhere parts of the catheter together. For instance, catheters are often constructed of two or more segments requiring a bonding and/or fusion method for sealing the segments together. For instance, catheter may be constructed of two or more shafts such as an outer shaft and an inner shaft, where the two shafts are then bonded together.

Other applications where adhesives might be used include bonding the manifold to the catheter shaft at the proximal end of the catheter, bonding of the guide wire port to the catheter shaft, for bonding a soft tip to the distal end of a catheter shaft, for bonding socs, for bonding marker bands, for bonding hypotubes to a polymeric tube, and so forth.

There remains a need in the art to be able to ascertain whether or not the adhesive has been accurately and properly applied to the medical device and at a precise location on the device, and whether or not a quality seal has been formed, especially in the case of bonding a catheter balloon to a catheter.

SUMMARY OF THE INVENTION

The present invention relates to the use of fluorescent dyes in adhesives used for various bonding applications in intraluminal medical devices, in particular, catheter assemblies. The fluorescent dyes allow the adhesive bond to be easily inspected for the bond quality without destruction of the bond and/or substrates.

Use of these fluorescing agents makes it easy to see exactly where the adhesive is being applied and to improve the accuracy of the application, particularly where operators are inexperienced. Because the adhesives used on these medical devices are typically clear and colorless or substantially so, are typically applied by hand, and the devices are typically quite small, it can be very difficult to accurately apply adhesive at the desired location on the device. The addition of a fluorescing agent, however, makes the bond visible under UV light thus allowing easy inspection of the bond.

More particularly, the present invention relates to an intraluminal medical device comprising at least two substrates or components of the same or a different material wherein the at least two substrates are bonded together with an adhesive comprising a fluorescing agent which fluoresces at a wavelength between about 200 nm and about 800 nm. The fluorescing agent is preferably a derivative of benzoxazole, a derivative of pyrene, a derivative of naphthalene, or some mixture thereof.

Even more particularly, the present invention relates to an intraluminal medical device comprising an elongated tubular member having a proximal end and a distal end and an inflatable balloon member located at the distal end of the tubular member and extending distally therefrom. The balloon member also has a proximal end and a distal end, and is made of a flexible material. The elongated tubular member and the inflatable balloon member are bonded together with an adhesive comprising a fluorescing agent resulting in an adhesive that fluoresces upon exposure to an ultra-violet light source.

The present invention further relates to stent delivery system comprising a stent delivery catheter and at least one stent retaining sleeve, the stent retaining sleeve being fixedly attached to the stent delivery catheter with an adhesive comprising at least one fluorescing agent. The adhesive fluoresces when exposed to ultraviolet radiation.

The present invention further relates to a method of detecting an adhesive bond in an intraluminal medical device having multiple substrates of the same or different materials, comprising the steps of adding a fluorescing agent to an adhesive composition, applying the adhesive composition to an intraluminal medical device where the adhesive composition forms an adhesive bond between substrates on the intraluminal medical device, irradiating the adhesive with a source of energy capable of inducing the emission of ultraviolet radiation having a wavelength of about 200 nm to about 800 nm, and observing the emitted ultraviolet radiation to determine the presence and location of said adhesive.

The fluorescing agent may be a benzoxazole derivative, a naphthalene derivative, a pyrene derivative, or some mixture thereof.

BRIEF DESCRIPTION OF THE SEVERAL VIEWS OF THE DRAWING(S)

DETAILED DESCRIPTIONS OF THE PREFERRED EMBODIMENTS

While this invention may be embodied in many different forms, there are described in detail herein specific preferred embodiments of the invention. This description is an exemplification of the principles of the invention and is not intended to limit the invention to the particular embodiments illustrated.

The fluorescent adhesives of the present invention can be used to bond any of the various parts of a catheter delivery device to one another. Specific applications include bonding of the stent retaining sleeves to the catheter shaft, bonding a dilatation balloon to the catheter shaft, bonding a hypotube to a polymeric catheter shaft, bonding the manifold to the catheter shaft at the proximal end of the catheter, bonding of the guide wire port to the catheter shaft, bonding marker bands to various components of the catheter delivery device, and so forth.

Further, as catheters are often constructed of two or more segments, an adhesive can be used to bond these segments together. For instance, the distal end of a catheter shaft may be constructed of a more flexible material than the proximal end of the catheter shaft. As these two segments are made of different materials, an adhesive can be used to secure them together. Also, a catheter may have an outer shaft and an inner shaft wherein the two shafts are then bonded together.

Figure 1:
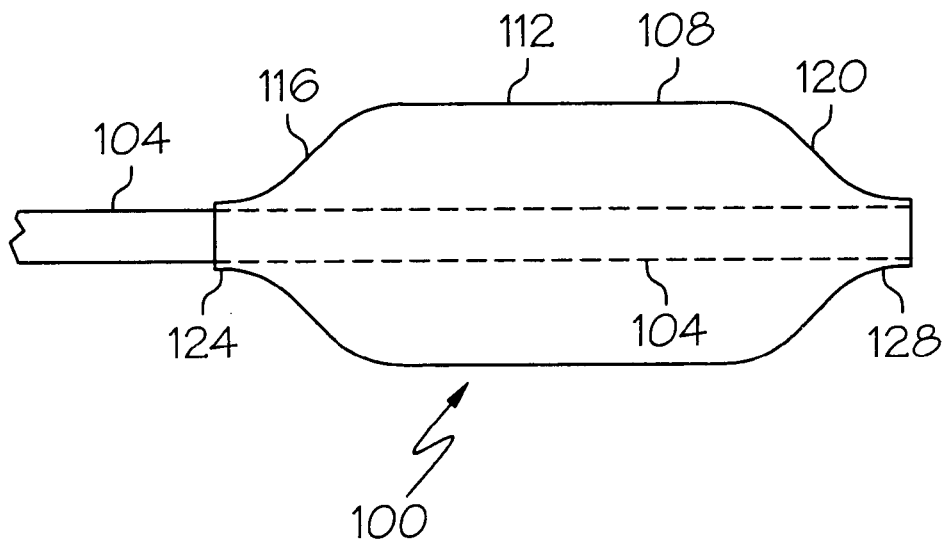
FIG. 1 shows a side elevational view of the distal end of a balloon catheter.

Turning to the drawings, the distal end region of a balloon catheter is shown generally at 100 in FIG. 1. The balloon catheter includes an elongate and pliable length of catheter tubing 104 constructed of a body compatible polymeric material such as a polyester. Desirably, a polyester elastomer such as Hytrel® may be used. Other suitable materials include polyolefins, polyamides and thermoplastic polyurethanes, and copolymers of these materials. A balloon 108 surrounds catheter tubing 104 along the distal end region. The balloon is shown in its fully expanded configuration, as when the balloon contains a fluid, supplied under pressure to the balloon interior through a balloon inflation lumen (not shown) open to the proximal end of catheter tubing 104 and to the balloon interior.

Fully expanded, balloon 108 includes a main body region 112, disposed about catheter tubing 104, and with a diameter substantially larger than that of the tubing. The appropriate balloon and catheter tubing diameters vary, depending upon factors such as the size of the vessel or other body cavity, and the procedure involved. At opposite ends of main body region 112 are a proximal cone 116, and a distal cone 120. The proximal cone terminates in a proximal neck region 124. The inner diameter of neck region 124 is substantially equal to the outer diameter of catheter tubing 104 in the region of the proximal neck to provide an interface region along which the interior surface of neck region 124 and the exterior surface of catheter tubing 104 confront one another and are contiguous.

Distal cone 120 similarly terminates in a distal neck region 128. The distal neck also has an inner diameter substantially equal to the outer diameter of catheter tubing 104 in the region of the distal neck. Consequently, the diameter of distal neck 128 typically is less than the inner diameter of proximal neck 124 because the catheter tubing is narrower along the distal neck due to the termination of the balloon inflation lumen proximally of distal neck 128.

Dilatation balloon 108 is desirably made from made from PET (polyethylene terephthalate). Other suitable materials include polyolefins such as polyethylene and polypropylene for instance, polyvinyl chloride, Surlyn® polyethylene ionomer copolymer, Pebax® polyamide-polyether-polyester block copolymer, PBT (polybutylene terephthalate), poly (butylene terephthalate)-block-poly(tetramethylene oxide), Arnitel® copolyetherester based on polybutylene terephthalate (PBT)/PTMO, Hytrel®, polyetherether ketone (PEEK), Teflon® polytetrafluoroethylene (PTFE), nylon (for example, nylon 12), and their copolymers as well as other polyolefins and silicone elastomers. Other suitable balloon materials are disclosed in PCT publication WO 97/32624 and commonly assigned U.S. application Ser. No. 08/926905. More generally, suitable materials include a polymeric material that is sufficiently pliable or formable to readily achieve the enlarged configuration, yet is relatively inexpansible, tending to maintain the configuration shown in FIG. 1 under increased fluid pressure within the balloon. Of course, the material should be biocompatible.

Other materials suitable for making both catheters and balloons are discussed in U.S. Pat. No. 6013728 to Chen et al. incorporated by reference herein in its entirety.

Figure 2:
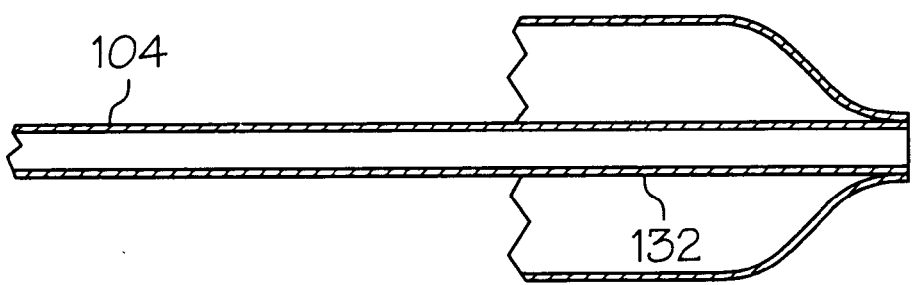
FIG. 2 shows an enlarged cross-sectional view of a portion of the balloon catheter of FIG. 1.

FIG. 2 is an expanded view of a portion of the same balloon catheter as shown in FIG. 1.

Figure 3:
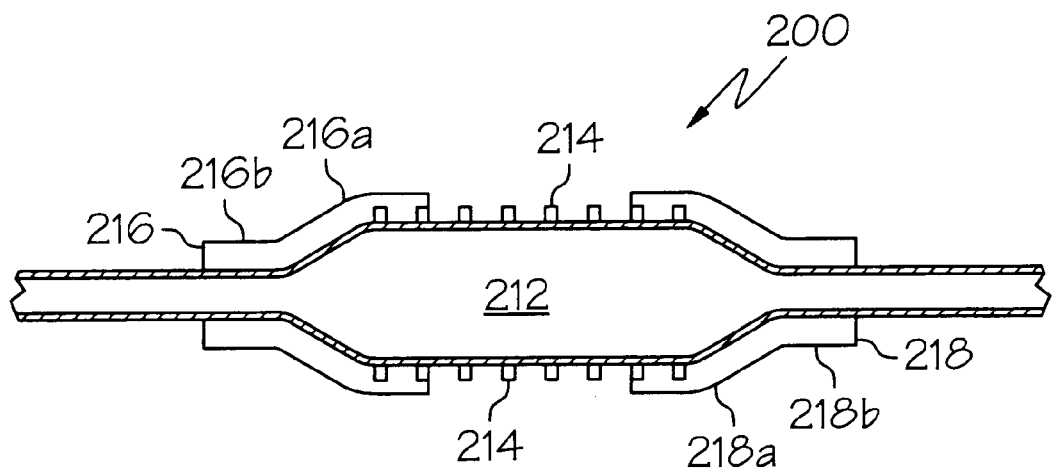
FIG. 3 is a side elevational view of a stent delivery catheter.

FIG. 3 illustrates generally at 200, a stent delivery catheter having an expandable portion or balloon 210. The expandable portion may be an inherent part of the catheter, or alternatively may be a separate balloon which is affixed to the catheter with the adhesives of the present invention as is shown in FIGS. 1 and 2. Disposed about the balloon 212 is a stent 214 as shown. Stent 214 may be any stent type capable of being delivered by a stent delivery catheter 200. Such stents may be either self-expanding or balloon expandable.

Attached to the catheter 200 are a pair of sleeves 216 and 218. The sleeves each include a first portion, 216a and 218a. When the balloon 200 is in the non-inflated state first sleeve portions 216a and 218a overlay the ends of balloon 212 as well as the ends of stent 214 as shown. Sleeves 16 and 18 also include respective second portions 216b and 218b. Regardless of the state of the balloon 212, non-inflated or inflated, second sleeve portions 216b and 218b are fixedly attached to catheter 210 with the adhesive system of the present invention. This involves applying the fluorescent adhesive between the catheter and sleeve at the sleeve portions 216b and 218b.

The stent retaining sleeves are typically manufactured of a polymeric material as well, and preferably the stent retaining sleeves are comprised of an elastomeric polymer system. This elastomeric polymer system may be comprised of an elastomer itself, or it may be a blend of polymers in which one or more of the polymers itself is not elastomeric but when blended produce an elastomeric system.

Figure 4:
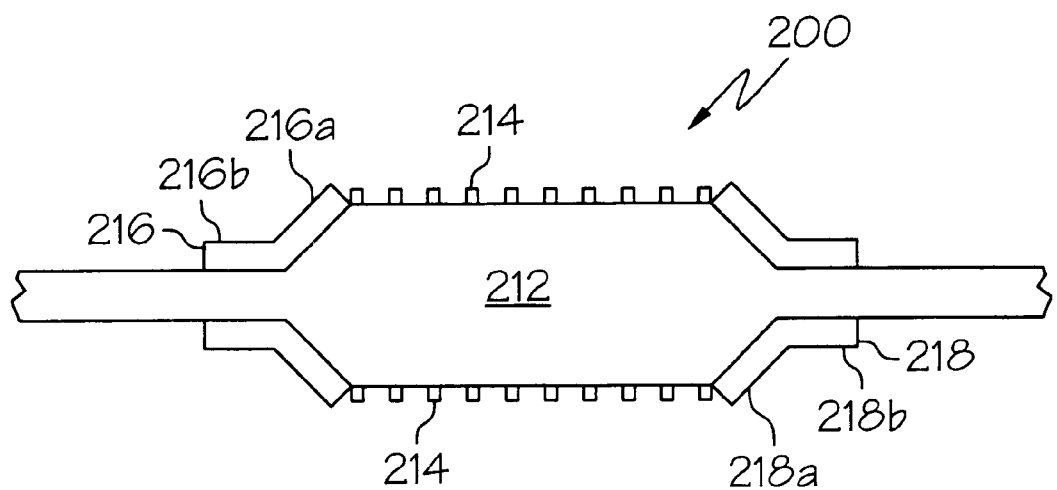
FIG. 4 is shows the same stent delivery catheter of FIG. 3 wherein the balloon has been inflated to its expanded state, thus releasing the stent retaining sleeves which allow the stent to expand as well.

FIG. 4 illustrates the same stent delivery catheter as FIG. 3 wherein the catheter balloon 212 is in its inflated state, and the pair of sleeves 216 and 218 have released stent 214.

The present invention involves the use of an adhesive system having a fluorescent dye or fluorescing agent that allows for easy inspection of the bond quality for bonding the various parts of a catheter device. The fluorescing agent provides the adhesive with fluorescence upon exposure to an ultraviolet radiation source.

The adhesives useful herein include any of those that are useful for adhering to materials used in medical devices. Typically, such adhesives are liquid and reactive or curable in nature. Examples of useful adhesives include cyanoacrylates, polyurethanes, epoxies, and so forth. Both one and two part adhesives may be used in the present invention.

Examples of cyanoacrylate adhesives useful herein include those based on esters formed by reacting α-cyanoacrylic acid with an alcohol. The ester constituent which is derived from the alcohol may be an alkyl group containing about 1 to 12 carbon atoms. The $C_1$–$C_2$ alkyl group may be non-substituted or substituted by a constituent such as a halogen atom, an alkoxy group, a straight-chain or branched-chain alkenyl group containing about 2 to 12 carbon atoms, an alkynyl group containing about 2 to 12 carbon atoms, a cycloalkyl group, an aralkyl group or an aryl group. Examples of constituents such as these include methyl, ethyl, n-propyl, isopropyl, n-butyl, isobutyl, pentyl, hexyl, allyl, methallyl, crotyl, propargyl, cyclohexyl, benzyl, phenyl, cresyl, 2-chloroethyl, 3-chloropropyl, 2-chlorobutyl, trifluoroethyl, 2-methoxyethyl, 3-methoxybutyl and 2-ethoxyethyl radicals. These adhesives, in combination with a bis-benzoxazoylyl fluorescing agent, are described in U.S. Pat. No. 4751020 incorporated herein by reference in its entirety.

Other useful cyanoacrylate adhesives are described in U.S. Pat. No. 4035334 incorporated by reference herein in its entirety. These adhesives are described as comprising a major proportion of 2-ethyoxethyl-α-cyanoacrylate and a minor portion of polyvinyl-n-butyl ether as measured in percent by weight.

More specific examples of adhesives useful in medical device applications include UV curing adhesives available from Dymax® Corp. in Torrington, Conn. Dymax® makes several lines of UV curing adhesives including the Ultra Light-Weld® line. Specific adhesives for catheter bonding include the "CTH" line of adhesives available from Dymax® such as 201-CTH, 202-CTH, 203-CTH, 204-CTH, and so forth. Other Dymax® adhesives useful herein which includes flexible adhesives, such as urethane oligomer/methacrylate monomer blends which can be ultraviolet curable such as Dymax 138-M std.

Another example of an adhesive useful for medical device applications is Loctite® 4011, a UV-curable ethyl cyanoacrylate adhesive available from Loctite Corp. in Rocky Hill, Conn. Other useful adhesives are supplied by the H. B. Fuller Co. in St. Paul, Minn. including one and two-part epoxy systems, one and two-part polyurethanes, and so forth.

The fluorescent dyes useful herein include any dyes that may be added to adhesives to provide fluorescence to the adhesive. These fluorescent dyes are useful in small amounts as opposed to those colorants that can be seen with the naked eye which typically require higher amounts which can negatively impact the performance of the adhesive. For medical applications, it is also preferable that the fluorescent dyes be clear and colorless to the naked eye, or nearly clear and colorless. Preferably, the dyes are soluble in oil.

Dyes other than those having oil solubility may be used but may require a solvent in order to achieve a uniform solution with the adhesive. Solvents preferable for use herein include those that are substantially insoluble in water including substantially water insoluble ketones such as methyl ethyl ketone (MEK), alkyl acetates such as ethyl acetate, chloroform, methylene chloride, tetrahydrofuran, acetone, and so forth. While the use of a solvent is an option, this is a less desirable route. The addition of solvent can impact the adhesive in one or more of several adverse ways. The addition of a solvent may decrease the adhesive cure time due to the additional time required to evaporate the solvent, or the solvent may itself react with the adhesive thus changing the adhesive's mechanical properties, or even prevent a full cure.

Examples of useful fluorescent dyes and fluorescing agents including FLUORESCEIN® (dye content ~95%) and FLUORESCENT BRIGHTENER 28 FREE ACID fluorescent dye, both available from Sigma-Aldrich Corp., benzoxazoles derivatives such as Uvitex® OB (bis-benzoxazolyl) available from Ciba Specialty Chemicals in Basel, Switzerland; Blankophor® CA 4410 available from Bayer Corp. in Pittsburgh, Pa. (parent company is Bayer AG in Germany); Fibers, Additives and Rubber Division; pyrenes including aminocoumarin conjugates, in particular dialkylaminocoumarin pyrenes, such as ALEXA FLUOR® 350 (carboxylic acid succinimidyl ester) and AMCA-X Dyes (succinimidyl ester); naphthalene derivatives such as N,N-dimethylamino-5-propionylnaphthalene; succinimidyl ester mixed isomers (i.e. of sulforhodarnine 101) such as RHODAMINE RED( (or TEXAS RED-X®) available from Molecular Probes, Inc. in Eugene, Oreg.; and so forth. Mixtures of the fluorescing agents are also useful herein.

UVITEX® fluorescing agents, benzoxazole derivatives, find particular utility in the present invention are available from Ciba Specialty Chemicals in Tarrytown, N.Y. UVITEX® OB, a 2,5-(di-5-tert-butylbenzoyl)thiophenate, is a particular example of a useful fluorescing agent available from Ciba Specialty Chemicals.

Useful fluorescing agents also include other benzoxazole derivatives such as HASTALUXV KCB, a 2,2-(1,4-Naphthalenediyl)bis-benzoxazole; and the EASTOBRITE® line available from Eastman Chemical Co. in Kingsport, Tenn., including EASTOBRITE(® OB-1, a 2,2'-(1,2-ethenediyldi-4,1-phenylene)bisbenzoxazole.

Water soluble fluorescing agents include, but are not limited to, those sold under the tradename of FLUORESCEIN® dyes, although useful herein are less desirable than some of the oil soluble dyes because they typically fluoresce less brightly. However, water soluble dyes may be useful when first dissolved in a solvent, and then subsequently mixed with the adhesive in order to achieve a more uniform mixture of dye and adhesive. Examples of useful solvents include methyl ethyl ketone, ethyl acetate, chloroform, methylene chloride, tetrahydroftiran, and acetone.

Other solvents including the short to medium chain length alcohols, including isopropyl alcohol, and water, may be used to dissolve the Fluorescein® dyes, but are less desirable because they too lack good solubility with the adhesives typically useful herein.

The fluorescing agents are typically added to the adhesive in an amount of about 0.001 to about 2%, preferably, about 0.005 to about 1%, and more preferably about 0.02% to about 0.5% by weight of the adhesive.

The fluorescent adhesives of the present invention can be used to bond various substrates on a medical device. In particular, for a stent delivery catheter, the adhesives can be used to bond the balloon to the catheter shaft, the stent retaining sleeves to the catheter shaft, and so forth. The substrates bonded may be comprised of the same, or of a different material. Any of the polymeric materials noted above are commonly employed in the manufacture of these devices.

The adhesives and method of the presence invention allow for easy detection of the adhesive bond. Fluorescence measurement systems typically consist of a source of energy for excitation such as an emission monochromator or spectrograph, and a detector device. The monochromator typically allows for a selection of excitation wavelengths. Most fluorescence measurements can be accomplished with short-focal-length monochromators for both excitation selection and emission measurements.

Any source of energy which will activate the fluorescing agent may be employed in the present invention. Suitable energy sources for use in the present invention include ultraviolet (UV) radiation, electron beam radiation, particle beam radiation, visible light, lasers (e.g. argon lasers), and so forth. Although visible light is acceptable, typically the fluorescing agents that respond to visible light must be added to the adhesive in higher amounts, resulting in both coloration of the adhesive, and the possibility of negatively impacting the adhesive bond.

The band width of light used may be from about 0.5 to about 10 mm. A preferred ultraviolet light source is an ultraviolet lamp manufactured by Cole-Parmer Instrument Co. in Vernon Hills, Ill. capable of emitting different wavelengths such as 254, 312, 365 nm, and so forth. The intensity ranges from about 340 to about 3400 $\mu$w/cm$^2$). Any detector capable of detecting energy having a wavelength in the ultraviolet region and lower visible region of the spectrum can be used in the present invention.

The present invention contemplates that the apparatus for detecting fluorescence can be used either on a production line, or in a laboratory setting. The present invention also contemplates the addition of a digital camera, and a data processing computer and program for viewing the adhesive bond and for analyzing the physical characteristics of the bond.

The wavelength emitted by the adhesive and detected by the detector device will vary depending on the dye or fluorescing agent used, but will generally vary from about 200 to about 800 nm for the UV-Vis region. Preferably, the energy source used in the present invention will include the UV spectral region, and the luminescent effect will usually be that of fluorescence. The emitted wavelength in this region will more typically be from about 250 to about 450 nm, and most typically from about 250 nm and about 400 nm if a UV energy source is provided.

As noted above, while dyes or agents having detectable wavelengths above 400–500 nm may be used, they are not preferable for use because typically a higher concentration must be used. This higher concentration can negatively impact adhesive characteristics, and colors the adhesive.

The apparatus may be adjusted to detect only those selected wavelengths that are emitted, or it may detect the whole spectrum.

In the broadest sense, the apparatus and method of the present invention can be used to simply observe the presence and location of the adhesive bond. Or more accurately, it can be used to confirm that the amount of adhesive used is correct. This involves measuring the intensity of the emitted radiation with a detector device (as noted above, any detector capable of detecting wavelengths in the range of 200 nm to 800 nm can be used) and comparing it to a predetermined reference value. In order to quantitate the adhesive bond, the computer should be precalibrated using the predetermined reference value which then allows a comparison of the measured intensity of the test adhesive to the predetermined reference value. If the values are different, this may be indicative of the fact that the amount of adhesive is incorrect. Furthermore, the computer can be equipped with an alarm to alert the operators to an unacceptable variation in the monitored adhesive.

A suitable digital color autofocus camera system for use herein is one manufactured by TechniQuip located in Livemore, Calif. The camera is equipped with a color monitor and a high resolution color video printer both made by Sony Corp.

EXAMPLES

Example 1

FLUORESCEIN® available from Sigma-Aldrich Corp. was mixed with Loctite® 4011 ethyl cyanoacrylate adhesive but was not soluble with the adhesive. Under UV light, the mixture did not exhibit any signs of fluorescing.

The FLUORESCEIN® was then dissolved in ethyl acetate solvent and subsequently mixed with Loctite® 4011. Fluorescein® dissolved readily in water or in isopropyl alcohol. However, such solvents, being nonsoluble in oil, also did not readily mix with Loctite® 4011 and consequently adhesive and the fluorescing agent remained insoluble, the mixture resulting in a white precipitate when mixed. The adhesive cured, but had a chalky, white appearance.

Solvents in which Fluorescein was successfully dissolved and mixed readily with the adhesive to produce a uniform solution included MEK, ethyl acetate, chloroform, methylene chloride, tetrahydrofuran and acetone.

Example 2

Fluorescent Brightener 28 Free Acid fluorescent available from Sigma-Aldrich Corp. was readily soluble in and mixed uniformly with Loctite® 4011 ethyl cyanoacrylate adhesive. The ingredients were mixed on a magnetic stirplate for 2 hours. Dye was added to the adhesive at concentrations of 0.3%, 0.2%, 0.1% and 0.05%. The ingredients produced uniform mixtures that fluoresced under UV light.

The mixtures were placed between glass slides, allowed to cure, and observed for fluorescence using a UV light at a wavelength of 365 nm. When the concentration of the fluorescent dye was increased from 0.05% to 0.3%, the image brightness increased.

The adhesives were then used to bond hubs. It was difficult to observe any fluorescence beneath the hub, but excess adhesive, if any, could be visualized outside the hub.

Bond strengths were measured using an Instron method to determine if the dye was affecting the adhesive cure times. POC film strips, 1.5×0.5 in., were bonded together with an overlap of 0.5×0.5 in. The bonds were cured using various time intervals, were pulled apart, and the peak force required to pull the bonds apart was recorded. None of the bonds failed.

A 90° peel test was conducted on an Instron using a 20 lb load cell, a 1 inch gauge length and a speed of 1 inch per minute.

Two sets of examples were tested. Loctite® 4011 was tested alone without any fluorescing agent, and then 0.2% Fluorescent Brightener 28 Free Acid fluorescing agent was added to Loctite® 4011. The following results were obtained at various cure times.

TABLE 1

Bond Strengths

| Cure Time | Loctite ® 4011 | Loctite ® 4011 + 0.2% Flourescent Brightener 28 |
|---|---|---|
| 5 seconds | 17.97 lbs | 19.9 |
| Observations | film strip slipped out of bottom groups | set for maximum of 20 lb load cell |
| 30 seconds | 19.9 lbs | 19.9 |
| Observations | POC film started to fail at a notch in the side of the film | set for a maximum of 20 lb load cell |
| 45 seconds | 18.86 lbs | 19.9 |
| Observations | film strip slipped out of bottom grips | set for a maximum of 20 lb load cell |
| 1 minute | 15.22 lbs | 19.9 |
| Observations | film strip slipped out of bottom grips | set for a maximum of 20 lb load cell |

Example 3

A hub tensile test was conducted using the stent tensile fixture and shims with 0.28 inch ID. One unit was tested for hub tensile. The hub was bonded with Loctite® 4011 cyanoacrylate adhesive with 0.05% Fluorescent Brightener 28 Free Acid dye. Failure occurred in the shaft material next to the hub bond at a force of 1.461 lbs.

Example 4

An adhesive containing a fluorescing agent was prepared by mixing 0.05 g of Uvitex® OB, bis-benzoxazolyl fluorescent compound available from Ciba Specialty Chemicals, in 5 ml of solvent, and then mixing the solution with a two-part polyurethane adhesive, UR-3507, available from the H.B. Fuller Co. in St. Paul, Minn.

Uvitex(V OB, 0.5 g, was first dissolved in several solvents to determine which it was most soluble in. The results from this test are found in the following table.

TABLE 2

| Solvent (5 ml) | Comments |
|---|---|
| isopropanol | Uvitex ® OB did not dissolve |
| acetone | Uvitex ® OB did not dissolve |
| heptane | Uvitex ® OB did not dissolve |
| methyl ethyl ketone | Uvitex ® OB was mostly dissolved |
| ethyl acetate | Uvitex ® OB was mostly dissolved |

The saturated solution of the Uvitex® OB in ethyl acetate was then added to the two-part adhesive. The fluorescing agent was added to both part A and part B of the two-part adhesive in an amount of 0.5 g of the Uvitex® OB/ethyl acetate solution to 3 g of part A and 0.5 g of the Uvitex®& OB/ethyl acetate solution to 3 g of part B. The mixture with part B had a paste-like appearance.

Part A, 1.6 g, and part B, 1 g, were then mixed together. A 3 cc syringe was filled with the adhesive/fluorescing agent blend which was then used to bond some balloon and catheter parts. The cure time was about 5 hours. The adhesive fluoresced under ultraviolet radiation.

The whole procedure was repeated using Uvitex® OB powder added directly to the adhesive rather than first dissolving it in solvent.

The fluorescing agent was added to both part A and part B of the adhesive in an amount of 0.0052 g Uvitex® OB added to 1.6 g of part A and 0.0052 g of Uvitex® OB added to 1 g of part B. The two parts were added together and mixed well. A 3 cc syringe was filled immediately with the mixed adhesive and used within 10 minutes. Balloon and catheter parts were then bonded. The cure time was approximately 4 hours after which time the adhesive exhibited good fluorescence.

The experiment was repeated. This time, part A and part B, each having 0.0052 g of Uvitex® OB, were mixed. Then, 0.2 g of Uvitex® OB powder was added to the polyurethane adhesive, 2.6 g, and mixed. The mixture was then placed into a 3 cc syringe. Balloon and catheter parts were bonded. The adhesive cured in about 4 hours and exhibited good fluorescence under a UV lamp.

The experiment was again repeated. Part A still had 0.0052 g of Uvitex® OB, but this time part B had none. Part A and part B were mixed. Then, 0.2 wt-% of Uvitex® OB was added to this mixture. The fluorescent adhesive was tested for bonding, cure and fluorescence as above. There were no notable changes in any of the properties.

The experiment was repeated, this time with part B having 0.0052 g of Uvitex(® OB and part A having none. The two parts were mixed. Then, 0.2 g of Uvitex® OB was added to the mixture. The adhesive was again tested for bonding, cure and fluorescence with no notable changes in any of the properties.

Each of these experiments was repeated without premixing parts A and B prior to the addition of 0.2 wt-% of Uvitex® OB. There were no notable changes in the properties of the adhesive.

Each of the above experiments was repeated with Uvitex® OB concentrations of 1.0 wt-% and 0.3 wt-% of the total mixture. The mixture appeared thicker prior to cure. Both concentrations exhibited fluorescence.

What is claimed is:
1. An intraluminal medical device comprising:
   a) an elongated tubular member having a proximal end and a distal end; and
   b) an inflatable balloon member located at the distal end of the tubular member and extending distally therefrom, said balloon member having a proximal end and a distal end, said balloon member being made of a flexible material;
wherein said elongated tubular member and said inflatable balloon member are bonded together with an adhesive comprising a fluorescing agent said adhesive fluorescing at a wavelength between about 200 nm and about 800 nm upon exposure to an energy source.

2. The medical device of claim 1 wherein said elongated tubular member is a catheter tube.

3. The medical device of claim 1 wherein said elongated tubular member is comprised of a polymeric material.

4. The medical device of claim 1 wherein said elongated tubular member is a polyester.

5. The medical device of claim 1 wherein said balloon is a catheter balloon.

6. The medical device of claim 1 wherein said balloon is comprised of a polymeric material.

7. The medical device of claim 1 wherein said balloon is selected from the group consisting of polyethylene terephthalate, polyethylene, polyvinyl chloride, polyethylene ionomer copolymers, polyamide-polyether-polyester block copolymers, polybutylene terephthalate, poly(butylene terephthalate)-block-poly(tetramethylene oxide), polyester elastomers, copolyetheresters, polyetherether ketone, polytetrafluoroethylene, polyamides, nylon, silicone elastomers, copolymers and terpolymers thereof, and mixtures thereof.

8. The medical device of claim 1 wherein said adhesive is selected from the group consisting of epoxies, cyanoacrylates and polyurethanes.

9. The medical device of claim 1 wherein said fluorescing agent is oil soluble.

10. The medical device of claim 1 wherein said fluorescing agent is selected from benzoxazole derivatives, naphthalene derivatives, pyrene derivatives, and mixtures thereof.

11. A method of detecting an adhesive bond in an intraluminal medical device having multiple substrates of the same or different materials comprising the steps of:
  a) adding a fluorescing agent selected from the group consisting of benzoxazole derivatives, naphthalene derivatives and pyrene derivatives to an adhesive composition;
  b) applying said adhesive composition to an intraluminal medical device wherein said adhesive composition forms an adhesive bond between substrates on said intraluminal medical device;
  c) irradiating said adhesive with a source of energy capable of inducing the emission of ultraviolet radiation having a wavelength of about 200 nm to about 800 nm; and
  d) observing said emitted ultraviolet radiation to determine the presence and location of said adhesive.

12. The method of claim 11 wherein said observing step further comprises detecting said emitted radiation with a detector device.

13. The method of claim 12 wherein said observing step further comprises measuring the intensity of said emitted radiation and comparing it to a predetermined reference value.

14. The method of claim 12 wherein said detector device further comprises an optical or digital camera which covers a preselected minimum area of said adhesive bond on said intraluminal medical device.

15. The method of claim 11 wherein said irradiating step induces the emission of ultraviolet radiation having a wavelength of about 200 nm to about 500 nm.

16. The method of claim 11 wherein said irradiating step induces the emission of ultraviolet radiation having a wavelength between about 250 and about 375 nm.

17. A stent delivery system comprising:
  a) a stent delivery catheter; and
  b) at least one stent retaining sleeve;
wherein said at least one stent retaining sleeve is fixedly attached to said stent delivery catheter with an adhesive comprising at least one fluorescing agent wherein said adhesive fluoresces when exposed to ultraviolet radiation.

18. The stent delivery system of claim 17 wherein said adhesive is selected from the group consisting of epoxies, cyanoacrylates and polyurethanes.

19. The stent delivery system of claim 17 wherein said fluorescing agent is oil soluble.

20. The stent delivery system of claim 17 wherein said fluorescing agent is selected from benzoxazole derivatives, naphthalene derivatives, pyrene derivatives, and mixtures thereof.

21. The stent delivery system of claim 17 wherein said stent retaining sleeves are comprised of an elastomeric polymer system.

22. An intraluminal medical device comprising at least two substrates of the same or a different material wherein said at least two substrates are bonded together with an adhesive comprising a fluorescing agent selected from the group consisting of derivatives of benzoxazole, derivatives of pyrene, derivatives of naphthalene, and mixtures thereof wherein said adhesive fluoresces at a wavelength of about 200 nm to about 800 nm upon exposure to an energy source said fluorescence allowing observation of the presence and location of the adhesive.

* * * * *